Figure 1:
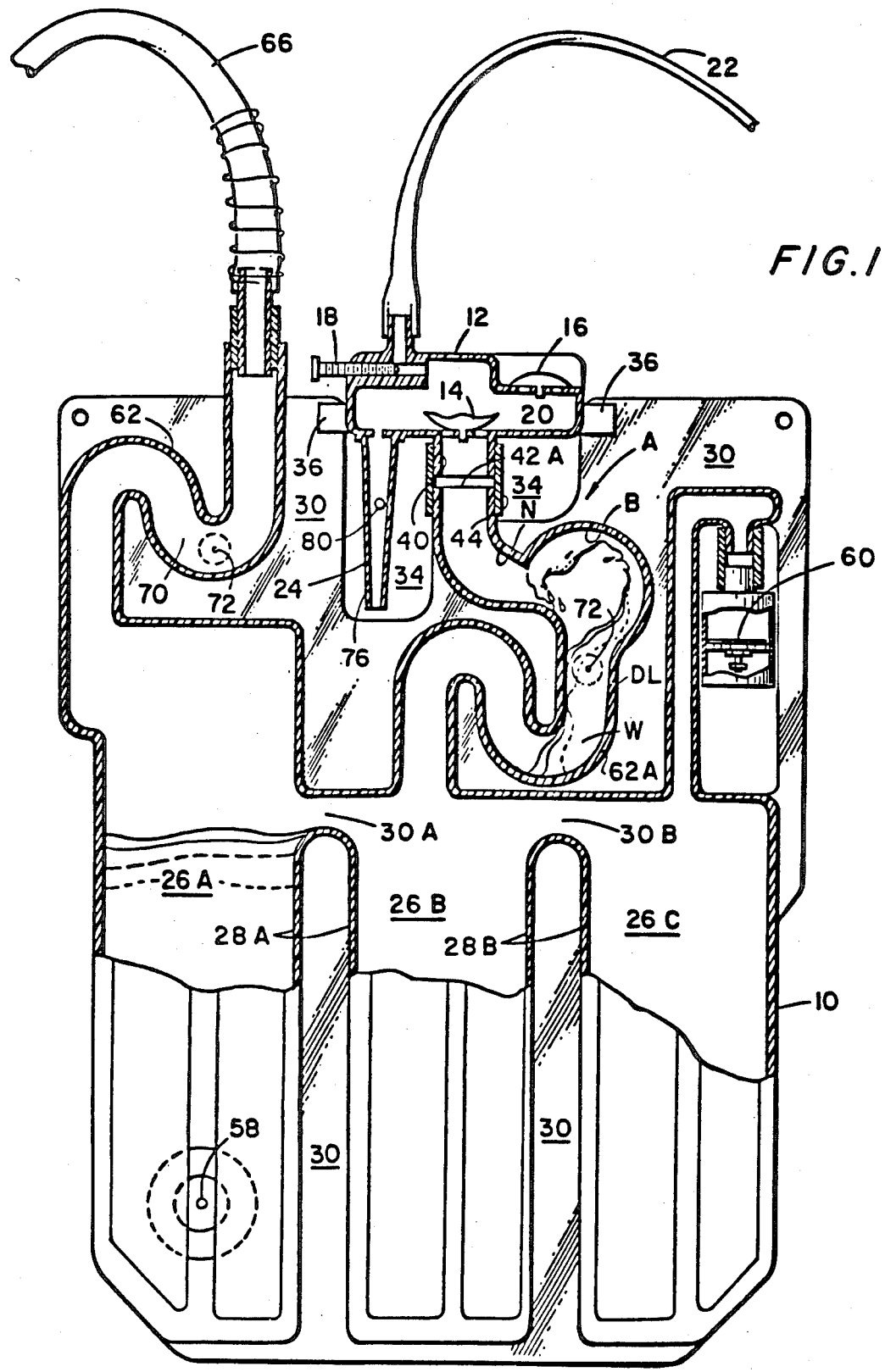

United States Patent [19]

Elliott et al.

[11] Patent Number: 4,715,856

[45] Date of Patent: Dec. 29, 1987

[54] AIR LEAK DETECTION SYSTEM FOR CHEST FLUID COLLECTION BOTTLES AND BLOW-OUT PREVENTION BAFFLE THEREFOR

[75] Inventors: Donald P. Elliott, Denver; William L. Halseth, Parker, both of Colo.

[73] Assignee: C. R. Bard, Inc., Murray Hill, N.J.

[21] Appl. No.: 765,315

[22] Filed: Aug. 13, 1985

Related U.S. Application Data

[63] Continuation of Ser. No. 381,161, May 24, 1982, Pat. No. 4,544,370.

[51] Int. Cl.$^4$ ............................................. A61M 1/00
[52] U.S. Cl. ................................... 604/321; 604/323; 604/324; 604/319
[58] Field of Search ............... 604/317, 319, 318, 320, 604/321, 322, 323, 325, 326; 37/205; 141/8, 35, 67; 433/87

[56] References Cited

U.S. PATENT DOCUMENTS

| 3,363,626 | 1/1968 | Bidwell et al. | 604/321 X |
|---|---|---|---|
| 3,363,627 | 1/1968 | Bidwell et al. | 604/321 |
| 3,559,647 | 2/1971 | Bidwell et al. | 604/321 |
| 3,683,913 | 8/1972 | Kurtz et al. | 604/321 |
| 3,861,390 | 1/1975 | Schachet | 604/321 |
| 4,018,224 | 4/1977 | Kurtz et al. | 604/321 |
| 4,261,362 | 4/1981 | Kurtz et al. | 604/321 X |
| 4,296,748 | 10/1981 | Kurtz et al. | 604/323 X |
| 4,312,351 | 1/1982 | Kurtz et al. | 604/321 X |
| 4,324,244 | 4/1982 | Kurtz et al. | 604/321 |
| 4,396,386 | 8/1983 | Kurtz et al. | 604/319 |
| 4,425,125 | 1/1984 | Kurtz et al. | 604/321 |
| 4,455,141 | 6/1984 | Todd | 604/319 |

OTHER PUBLICATIONS

"Understanding Underwater Chest Drainage", Cheesborough–Pond's, Inc., Greenwich, Conn., HPO-UW-D-LIT-376; Mar. 1976, p. 9.

*Primary Examiner*—William H. Grieb
*Attorney, Agent, or Firm*—Wolf, Greenfield & Sacks

[57] ABSTRACT

This invention relates to an improved chest fluid drainage bottle of the type having a fluid collection chamber connectable to receive fluid sucked from the patient's chest, the improvement consisting of an improved air leak detection system characterized by a fluid filled U-tube downstream of the air space overlying the fluid collecting chamber cooperating therewith to define an air leak detector substantially insensitive to small intermittent variations in upstream pressure while, at the same time, providing an observer with a reliable visual indication of a continuous upstream leak. The improvement also encompasses an anti-splash baffle adjacent the outlet of the U-tube effective to prevent the fluid therein from leaving same and, perhaps, entering the vacuum system upon the application of larger than normal intermittent upstream positive pressure surges.

5 Claims, 2 Drawing Figures

AIR LEAK DETECTION SYSTEM FOR CHEST FLUID COLLECTION BOTTLES AND BLOW-OUT PREVENTION BAFFLE THEREFOR

This application is a continuation of application Ser. No. 381,161, filed May 24, 1982, now U.S. Pat. No. 4,544,370, granted Oct. 1, 1985.

This invention relates to devices of the type described in U.S. application Ser. No. 156,920 filed June 6, 1980, now abandoned and entitled CHEST FLUID COLLECTION AND STORAGE BOTTLE WITH PRESSURE REGULATING AN AIR FLOW DETECTION AND REGULATING FEATURES. In this earlier application, a fluid filled U-tube was interposed between the patient's chest cavity and the collection chamber of the chest bottle which, under certain circumstances, of biphasic air flow could be misinterpreted by the user as an air leak. More specifically, the aforementiond U-tube responded to an air leak upstream thereof by revealing a stream of bubbles passing through the fluid contained therein and on down into the air space in the collection bottle above the chest fluids being collected.

The upstream fluid filled U-tube at the entrance to the fluid collection chamber served, and still serves, a valuable function in that the to-and-fro fluctuations of the fluid contained therein provide the observer with a clear and reliable indication that intra-thoracic pressure changes are being transmitted to the collection chamber. As a matter of fact, when used as recommended by carefully balancing the system pressure (negative) with that of the pleural cavity, the upstream U-tube is actually a very trustworthy air leak detector also. It was only when used in an unbalanced state that misinterpretations occurred. The upstream U-tube and the fluid collected therein does tend to back up a certain amount of fluid in the drainage tube leading from the patient when there is no air leak and this fluid standing up in the patient drain tube serves as an absolute indicator that no air leak is present because, when there is an air leak, the fluid level falls down to the U-tube and bubbles can then be seen passing downstream through the fluid trapped therein. Each measurement of the drainage volume requires that the fluid in the patient tube either be "milked" periodically or opened briefly to the atmosphere to allow the fluid to flow into the collection chamber but this minor inconvenience is far outweighed by the important function of detecting an air leak when present and responding to intra-thoracic pressure fluctuations.

It has now been found that this objectionable feature of the upstream fluid filled U-tube can be overcome by the simple, yet unobvious, expedient of either relocating it downstream of the large volume dead air space above the fluid collection chambers or, even better, supplementing it with a second fluid filled U-tube so located as to interpose this large volume of air that exists above the fluids being collected in the bottle between the fluid in the downstream U-tube and the patient. When this is done, the high negative pressures occurring in the thorax, particularly in labored breathing, which have in the past given rise to a biphasic bubbling in the upstream U-tube, and which have occasionally been misinterpreted by some as an air leak, will now be unable to draw air back across the downstream U-tube because of the very small air volume between the downstream U-tube and the main outlet valve. Any air bubbles seen moving upstream or backwards in the downstream U-tube would indicate a leak in the main outlet valve or related connections. A true air leak, on the other hand, will produce a steady downstream or forward flow of bubbles through the fluid in the downstream U-tube and the upstream one also if the system includes both.

Another incidental, but nonetheless significant, feature of the improved chest drainage system is that of providing what has already been denominated here as the "downstream U-tube" with baffling at the exit end thereof effective to intercept and return the fluid thereto in the circumstance of a sudden surge of upstream pressure such as might be caused by the patient coughing that would otherwise blow the fluid therefrom and out into the vacuum system, flow meter or other feature located downstream thereof. Thus, serious air leaks in the system or in the patient's pleural cavity of a magnitude sufficient to blow the fluid out of the upstream U-tube requiring that it either be primed or allowed to refill present no problem to the downstream one which will automatically respond by returning the fluid to its downstream leg before it can enter the control system.

It is, therefore, the principal object of the present invention to provide a novel and improved chest drainage apparatus.

A second object is to provide an apparatus of the character described which can be relied upon to detect an air leak in either the system or in the patient.

Another object is the provision of a baffled fluid trap within the downstream U-tube effective to intercept and return the fluid confined therein upon the application of instantaneous surges in pressure (air flow) that would ordinarily blow it out the downstream end.

An additional object is to provide an improved version of the earlier single U-tube fluid collection bottle containing two fluid filled U-tubes connected in series with one another and with the air space above the fluid collection chamber, one U-tube being upstream of the collection chamber as before while the second lies downstream thereof.

Further objects are to provide a chest drainage system that is simple, reliable, convenient, relatively inexpensive, one devoid of water seals that require priming and a unit of the class described that is decorative in appearance.

Figure 2:
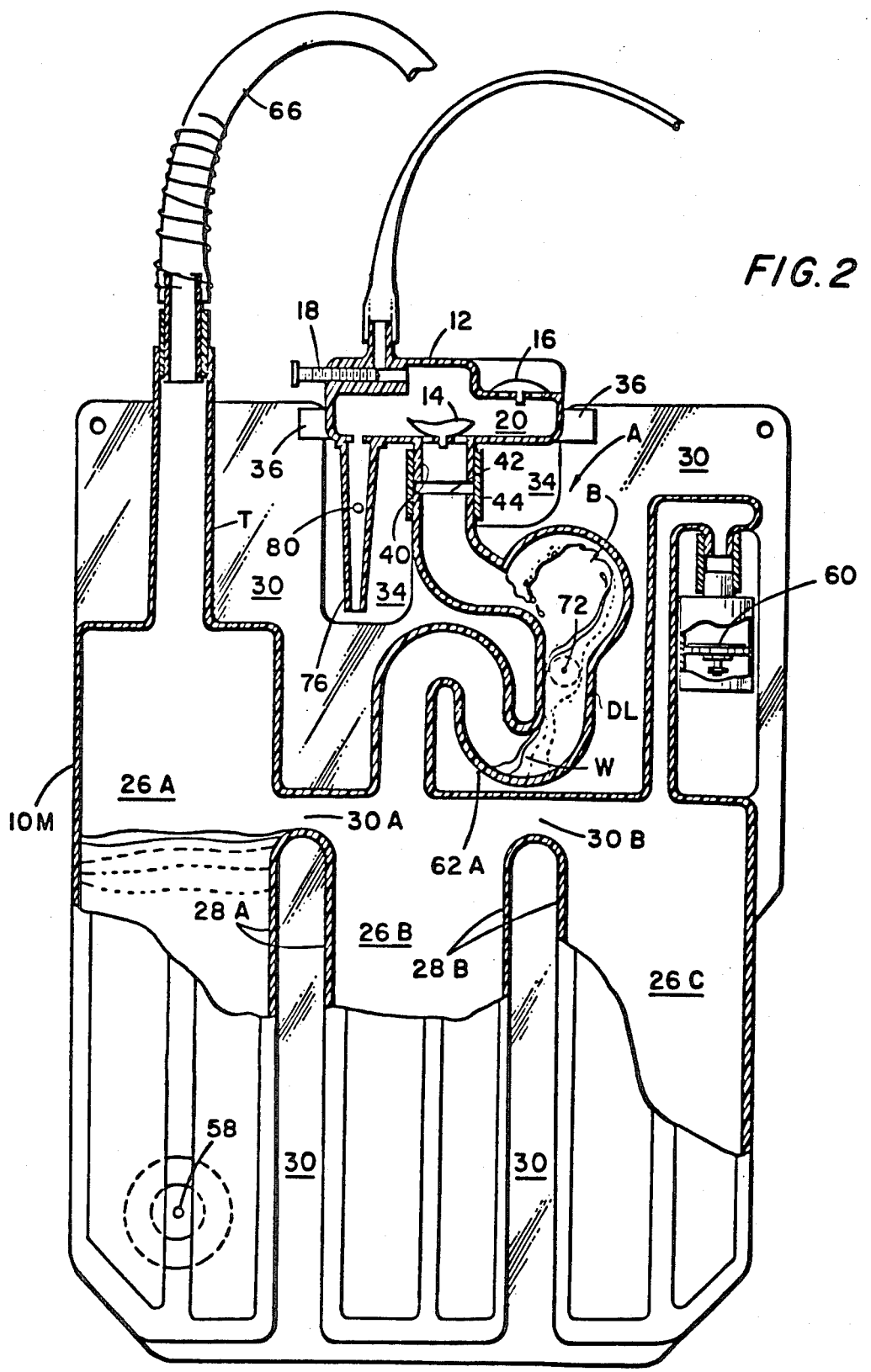

Other objects will be in part apparent and in part pointed out specifically hereinafter in connection with the description of the drawings that follows, and in which:

FIG. 1 is a side elevation, portions of which have been broken away and shown in section to more clearly reveal the interior construction of the improved chest drainage apparatus having a second fluid filled U-tube located downstream of the fluid collection chamber; and, FIG. 2 is a side elevation partly broken away and shown in section that is like FIG. 1 except that the upstream U-tube has been eliminated.

Referring next to the drawings for a detailed description of the present invention and, initially, to FIG. 1 for this purpose, bottle 10 together with the control subassembly 12 therefor can be seen to include each and every element of the earlier chest drainage system forming the subject matter of U.S. application Ser. No. 06/156,920, now abandoned and U.S. application Ser. No. 06/341,877, now abandoned previously noted. The improvements forming the subject matter of the instant application are, on the other hand, all to be found within a second U-tube subassembly which has been broadly identified herein by reference letter A in cooperation with the large dead air space above the fluid in the collection chambers immediately upstream thereof.

To be more specific, control subassembly 12 still incorporates the check valve 14, the positive pressure relief valve 16 and the control valve 18 that regulates the negative pressure in the system. The aforementioned valves all connect into the interior of air chamber 20 as does the negative pressure gauge 24.

Bottle 10, in the particular form shown, includes the series of three fluid collection chambers 26A, 26B and 26C separated from one another by partitions 28A and 28B. Opening 30A at the top of partition 28A allows fluid in chamber 26A to overflow into chamber 26B and opening 30B does the same for fluid passing between chambers 26B and 26C. The height of these partition walls in comparison to the overall height of the bottle is such that a dead air space always exists until the last chamber is full which has a volume greatly in excess of any air space in the discharge tube 22 or the patient's pleural cavity.

Subassembly 12 is shown connected as before to web 30 by means of clips 36 within notched out portions 34; however, the latter portions are essentially reversed end-for-end so that the negative pressure gauge 24 is now on the opposite side of check valve 14 so as to leave sufficient room beneath air chamber 20 to accommdate the second U-tube subassembly A as illustrated. Tubular air inlet 40 in the bottom of air chamber 20 aligns with the outlet 42 of second U-tube subassembly A of bottle 10 where hose 44 completes the connection therebetween. Labels 46 with liquid level observation slots 48 therein are shown glued or otherwise attached to the three fluid collection chambers 26. The location and function of resealalbe grommet 58 in the bottom of chamber 26A remains as before, namely, that of permitting fluids to be either withdrawn therefrom or introduced therein.

Negative pressure relief valve 60, likewise, functions in the same way it did in the earlier version of the unit to open and admit air from the atmosphere into the fluid-free air space above the fluid in collection chambers 26 whenever an abnormally high negative pressure condition is sensed. Valve 60 by limiting the negative pressure in the system to a predetermined level can be set to prevent trauma and injury to the delicate tissues of the mediastinum which would occur if it were to be sucked into the intake end of drainage tube 66.

Upstream U-tube 62 together with the small amount of fluid 70 contained therein still functions in the manner intended as both a visual indicator that the patient is still breathing and as an air leak detector despite the addition of another independent, and reliable leak detector in the form of the second or downstream U-tube subassembly A. In other words, upstream U-tube 62 and its associated fluid 70 do not lose their capacity to detect air leaks in the system when the pressure regulating valve 18 of control system 12 has been properly set to balance the negative pressure inside the patient's chest cavity just because a second leak detection system (subassembly A) answers this same need. What the latter subassembly does do is provide the surgeon or other operating roqm personnel with an independent and totally reliable leak detection system when U-tube 62 and its fluid 70 are giving out false indication of a leak due to the fact that pressure regulating valve 18 has been improperly set or some other anomalous condition is present like, for instance, the patient having labored or obstructed breathing.

Self-sealing ports 72 in both the upstream and downstream U-tubes perform the same function, specifically, the insertion or withdrawal of fluid. It should be noted, however, that the downstream U-tube 62A is not self-priming as was the case with upstream U-tube 62 but must, instead, be primed through its port 72. As such, downstream U-tube 62A will ordinarily not contain fluid drained from the patient's pleural cavity since it has no access thereto and no reason exists for priming same with other than distilled water W. For this same reason, resealable port 72 in the downstream U-tube 62A cannot, obviously, be used to draw samples of the chest fluid.

The fluid 70 in upstream U-tube 62 remains ineffective to form a fluid seal as in some of the prior art chest drainage systems operative to prevent the backflow of air into the patient. Instead, check valve 14 located in the control subassembly 12 at the inlet to chamber 20 prevents the return flow of air from the aforementioned chamber back into the dead air space in fluid collection chambers 26 above the fluids contained therein. Check valve 14 is actuated to its open position by a small negative differential pressure in chamber 20 as suction is applied to the latter by means of the institution's vacuum system represented by vacuum line 22. Pressure regulator 18 continues to function as a throttling valve operative to cut down the excessively high negative pressure capable of being generated by the institution's vacuum system to that which is compatible with the patient's own negative pressure system. If, perchance, a positive pressure should build up in chamber 20 which, if permitted to reach the air space above the fluid in chambers 26 by reason of its having blown out check valve 14, then positive pressure relief valve 16 takes over and dumps the excess pressure to the atmosphere thus preventing the backflow of both gas and the fluids contained in upstream U-tubes 62 from returning to the patient's chest cavity. The release point of valve 16 is set at a level far below that at which valve 14 will fail, of course.

The presence of the second or downstream U-tube 62A in the system has no effect one way or another on the function and/or operation of valves 14, 16 or 18, all of which lie downstream thereof. Negative pressure relief valve 60, of course, bypasses the downstream U-tube entirely and is, therefore, also uneffected thereby. The same is true of the negative pressure gauge 24 which still performs the same function in the system, namely, that of providing the operator with a visual indication of just what negative pressure exists within chamber 20 of the system into which it connects.

Having thus described the more significant elements of the predecessor chest drainage system and control mechanism therefor in their relation to one another and to the newly added downstream U-tube subassembly A, the latter and its various functions will now be set forth in detail. Before doing so, however, it would, perhaps, be helpful to understand some of the physiology involved and how various conditions are "seen" by this and other systems used for evacuating liquids and air from the pleural cavity. Air accumulating in the pleural cavity, so-called "pneumothorax", with no means of escape can lead to a build-up of intrapleural pressure (tension pneumothorax) which causes mediastinal shift that can be fatal if not recognized and controlled in time. Obstruction or pinching all of the tube leading to the vacuum source, the failure of the vacuum pump in the closed state or even a patient with an air leak beyond the capacity of the pump to handle can cause the aforesaid condition. It is, therefore, imperative that the physician be able to reliably and immediately detect a positive pressure build-up in the pleural cavity, regardless of its cause. While positive pressure relief valve 16 functions automatically to limit the positive pressure build-up to a predetermined small level, the fact that it has actuated may go undetected since it need only unseat a small fraction of an inch. Check valve 14, of course, functions in this circumstance to prevent the positive pressure built up in chamber 20 from reaching the patient and, therefore, the latter remains fully protected. Also, the pressure gradient will be such as to drive ball 80 of negative pressure gauge to the bottom of its tube 76 thus providing the operator with a visual indication that something is amiss. Note, however, that it is only when an abnormal positive pressure condition exists downstream of check valve 14 that this occurs. In other words, a positive pressure build-up upstream of check valve 14 such as might be initiated by the patient coughing, a true air leak or the patient being breathed mechanically would go undetected were it not for one or the other or both of the fluid filled U-tubes 62 and 62A. Of the various causes, the one to be feared, however, is an air leak in the patient's pleural cavity. Such an air leak will immediately show up as a flow of bubbles within the fluid 70 in upstream U-tube 62; however, if the patient is intermittently generating negative pressures exceeding that imposed on the dead space by the pressure regulator, then air can be drawn back across the upstream U-tube because of the large compliant air space over the collection chambers. This air drawn upstream or backwards during the negative pressure or inspiratory phase of respiration, can subsequently be forced downstream forwardly across the upstream U-tube during the positive pressure or expiratory phase of respiration. Such biphasic bubbling can be misinterpreted as an air leak when one exists. On the other hand, it can obscure a small air leak because the volume going in each direction cannot be quantified. The proper use of the present unit requires that the negative pressure imposed on the unit as indicated by the floating ball in the pressure regulator be increased to balance the maximum negative pressure generated by the patient so that this biphasic bubbling does not occur. For example, if the suction in the system regulated by valve 18 is not in balance with that which exists in the patient's chest, false indications of a leak can occur because bubbles may move through the fluid 70 in the upstream U-tube, not as a result of a leak at all, but rather, perhaps, because the patient is being "breathed" by a respirator which forces air into the lungs and they, in turn, force trapped air out of the chest into the collection system. It is only when the volume of air thus displaced becomes a significant fraction of the available air space between the patient and the upstream U-tube that this becomes a problem. Conversely, in accordance with the teaching found herein, if this displaced air can find its way into the large volume dead air space above the fluid collected in collection chambers 26, its effect will be cushioned and damped thereby to an extent where it will have very little noticeable effect, if any, upon the fluid W in the downstream U-tube 62A. Thus, when a system leak exists in discharge hose connecting the patient to the bottle, or the patient really does have an air leak, bubbles will still appear in the downstream U-tube signalling the need for remedial action. Also, sudden large increases in positive pressure such as are caused by a cough will not blow the fluid from the second U-tube but merely send it up against the dome-like baffle B where it is immediately returned to its former location.

As previously noted, downstream U-tube 62A is primed with water W through resealable port 72 to activate the leak detector which will then respond in the manner set forth above to provide the observer with a reliable visual indication of any leak in the system. Since the downstream U-tube is not self-priming as is the case with the upstream one, provision has been made for trapping the priming fluid W within the unit so as to prevent it from being blown past check valve 14 and up into chamber 20 if the patient should cough and thus bring about an abnormally high positive pressure in the air space above the fluid collection chambers. This is accomplished by providing downstream U-tube 62A with a splash dome B at the outlet thereof. This dome is located directly above the downstream leg DL of the U-tube in position to intercept any fluid exiting the latter. Its shape is such as to define a baffle effective to redirect any fluid impinging thereagainst back down into the U-tube before it can enter the laterally offset neck N thereof. Thus, any priming fluid blown out of the U-tube will strike the splash dome and drain back into the downstream leg DL thereof without ever entering offset neck N in the manner illustrated in FIG. 2. No such baffling is needed in the upstream U-tube because any fluid lost will immediately be replaced by the fluids drained from the patient's chest.

Briefly with respect to FIG. 2, it shows a modified bottle 10M identical in every respect to bottle 10 of FIG. 1 except that the upstream U-tube 62 has been eliminated and replaced by a straight inlet tube T. The ability of the leak detection subassembly A to reliably detect and provide the observer with a visual indication of any leaks in the system remains unimpaired by the deletion of the upstream fluid filled U-tube 62. All elements of the control subassembly 12, negative pressure relief valve 60 and other elements of the system remain unchanged and are so indicated by employing the same reference numbers and letters as were used in the description of FIG. 1. While the FIG. 2 version has the advantage of eliminating the need for "milking" blood and other fluids trapped upstream of the fluid in the upstream U-tube, these problems are considered of minor importance when compared with the advantages realized by having both the upstream and downstream U-tubes, therefore, in this sense, the double U-tube version of FIG. 1 is preferred.

What is claimed is:

1. An apparatus for draining a patient's chest cavity comprising a body including a closed collection chamber having an inlet at the upper end thereof for connection to a patient drainage tube permitting chest cavity fluid and air to drain directly through said inlet to provide direct unobstructed flow of air and fluid into said collection chamber, an air space above the collection chamber, an outlet from the collection chamber in communication with the air space, said body further including a combination negative pressure indicator and air leak detector assembly in turn including a reservoir positioned downstream of said collection chamber and having a liquid trap portion for receipt of an indicator fluid, said reservoir connected to said collection chamber by an upright column positioned intermediate said collection chamber and said reservoir and in turn connected to said outlet at the upper end thereof and to said liquid trap portion at the lower end thereof, and one-way valve seal downstream of the negative pressure indicator and air leak detector assembly acting as a seal to prevent air from entering back into the air leak detector but permitting air from the air leak detector to flow out the valve seal.

2. The apparatus according to claim 1, including means downstream of the one-way valve seal comprising a flow control valve connectable to a source of external suction, said flow control valve being operable to selectively control the level of suction being applied upstream of the one-way valve seal.

3. An apparatus for draining the chest cavity according to claim 2, wherein a positive pressure relief valve is provided.

4. An apparatus for draining the chest cavity according to claim 2, wherein a high negative suction relief valve is provided.

5. An apparatus for draining the chest cavity according to claim 1, wherein said collection chamber is a plurality of connected chambers.

* * * * *